United States Patent [19]

Hamanaka

[11] 4,192,759
[45] Mar. 11, 1980

[54] AUTOMOTIVE BRAKE FLUID COMPOSITIONS INCLUDING SEMIPOLAR BORATES AND HETEROBORATES

[75] Inventor: Hiroyoshi Hamanaka, Yachiyo, Japan

[73] Assignee: Toho Chemical Industry Co., Ltd., Tokyo, Japan

[21] Appl. No.: 925,600

[22] Filed: Jul. 17, 1978

[51] Int. Cl.$^2$ .............................................. C10M 3/48
[52] U.S. Cl. .................................................. 252/78.1
[58] Field of Search ..................... 252/78.1; 260/462 R

[56] References Cited

U.S. PATENT DOCUMENTS

| | | | |
|---|---|---|---|
| 3,625,899 | 12/1971 | Sawyer et al. | 252/75 |
| 3,637,794 | 1/1972 | Sawyer et al. | 260/462 R |
| 3,772,357 | 11/1973 | Hamanaka | 260/462 R |
| 4,116,846 | 9/1978 | Sato et al. | 252/78.1 |

FOREIGN PATENT DOCUMENTS 2438038 2/1975 Fed. Rep. of Germany.

Primary Examiner—Harris A. Pitlick
Attorney, Agent, or Firm—Karl W. Flocks

[57] ABSTRACT

Brake fluids of good quality which increase wet equilibrium reflux boiling point without increasing rubber swelling property and disperse or dissolve homogeneously the additives and metals extracted from rubber brake cups and cylinder pipes can be obtained by dissolving semipolar borates containing a bond represented by the formula,

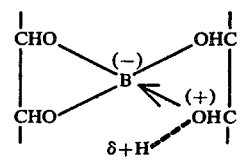

which can be a hybridized orbital between SP$^2$ and SP$^3$ with regard to boron atom and having at least two hydroxyl groups outside said bond and heteroborates comprising an SP$^2$ hybridized orbital and containing butyl group and methyl group in their molecule in polyalkylene glycol monoalkyl ethers comprising a C$_1$–C$_4$ alkyl group.

9 Claims, No Drawings

AUTOMOTIVE BRAKE FLUID COMPOSITIONS INCLUDING SEMIPOLAR BORATES AND HETEROBORATES

The present invention relates to brake fluid compositions for automobiles. More particularly, the invention pertains to brake fluid compositions for automobiles comprising borates having a semipolar structure, heteroborates containing butyl group and methyl group in their molecule and polyalkylene glycol monoalkyl ethers.

At present, an attempt has been made to obtain better brake fluids for automobiles having an increased wet equilibrium reflux boiling point by adding triborates comprising an $SP^2$ hybridized orbital to polyalkylene glycol monoalkyl ethers which are used as brake fluids for automobiles. (For example, U.S. Pat. No. 3,625,899). However, brake fluids comprising such combinations have still a defect in that they are inferior to brake fluids comprising only a polyalkylene glycol monoalkyl ether in rubber swelling property. In a rubber swelling property test, therefore, the zinc oxide and fatty acids extracted from the rubber cup form an undesirable suspension state. Also, in a metal corrosion test, the ingredients extracted from the rubber cup react further with metals to form an insoluble precipitate. There is the possibility that the formation of such a precipitate results in the clogging of a fluid pressure feed pipe line for a brake fluid on actual travel of automobiles.

Therefore, an object of the present invention is to obviate the defects of prior art brake fluid compositions for automobiles.

Another object of the invention is to provide brake fluid compositions for automobiles of good quality.

Another object of the invention is to provide brake fluid compositions for automobiles which can satisfy the second class, No. 2 standard of JIS K-2233 and DOT-4 grade of Federal Motor Vehicles Safety Standard (FMVSS No. 116).

The other objects and advantages of the invention will be apparent from the following description of the invention.

As a result of various studies, the present inventors have now reached an invention of obtaining brake fluids of good quality which increase wet equilibrium reflux boiling point (hereinafter referred to as "WET-ERBP") without increasing rubber swelling property and disperse or dissolve homogeneously the additives and metals extracted from rubber cups and cylinder pipes by dissolving semipolar borates containing a bond represented by the formula,

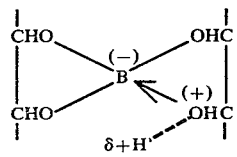

which can be a hybridized orbital between $SP^2$ and $SP^3$ with regard to boron atom and having at least two hydroxyl groups outside said bond and showing rubber compression properties (hereinafter referred to as "the appointed semipolar borates") and heteroborates comprising an $SP^2$ hybridized orbital and containing butyl group and methyl group in their molecule and showing a strong dissolving power (hereinafter referred to as "the appointed heteroborates") in polyalkylene glycol monoalkyl ethers comprising a $C_1$–$C_4$ alkyl group (hereinafter referred to as "the appointed polyalkylene glycol monoalkyl ethers").

With regard to the brake fluid compositions according to the present invention, there can be considered a mechanism that the ingredients extracted from a rubber cup and cylinder pipes are chelated with the appointed semipolar borates, and then dissolved in the appointed heteroborates, and finally homogeneously dispersed in the appointed polyalkylene glycol monoalkyl ethers, and thereby the precipitation of the ingredients can be prevented.

Thus, according to the present invention, there is provided brake fluid compositions for automobiles comprising as an effective ingredient a mixture of at least one of the appointed semipolar borates represented by the general formula,

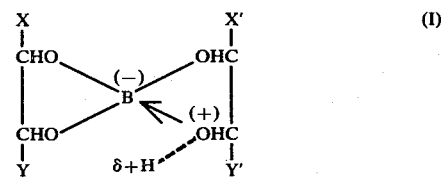

wherein X, X', Y and Y' each are hydrogen atom, a group of the formula,

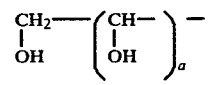

wherein a is 0, 1, 2 or 3, or a group of the formula,

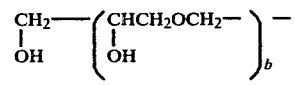

wherein b is 1 or 2 provided that at least two hydroxyl groups are present in X+X'+Y+Y', at least one of the appointed heteroborates represented by the general formula,

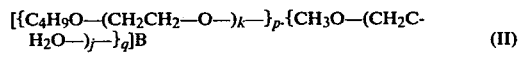

wherein p is a positive number of 1 to 3/2, q is a positive number of 3/2 to 2 and p+q is 3, k is a positive number of 1 to 3, and j is a positive number of 3 to 5, and at least one of the appointed polyalkylene glycol monoalkyl ethers represented by the general formula,

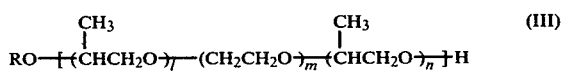

wherein R is a $C_1$–$C_4$ alkyl, l is 0 or a positive number of 3/2 or less, n is 0 or a positive number of 3/2 or less, and m is a positive number of 3 to 5 provided that there are the following relationship between l, m and n:

$$3 \leq (l+m+n) \leq 5$$

and $$0 \leq l + n/(l + m + n) \leq \tfrac{1}{3}$$

These materials are desirably mixed in quantities of 1-10% by weight of compounds I, 9-50% of compounds II and 40-90% of compounds III.

Here, the appointed semipolar borates can be obtained by the following three processes:

Process i

Two moles of at least one of polyhydric alcohols comprising vicinal hydroxyl groups (hereinafter referred to as "the appointed polyhydric alcohols") and one mole of boric acid are subjected to triesterification reaction.

Process ii

Two moles of at least one of the appointed polyhydric alcohols and one mole of at least one of lower alkyl triborates having 1 to 3 carbon atoms are subjected to triesterification reaction by transesterification.

Process iii

Four mols of at least one of the appointed polyhydric alcohols and one mole of boric anhydride are subjected to triesterification reaction.

The appointed semipolar borates are exemplified by bisglyceryl borate, bisxylityl borate, bissorbityl borate, bismannityl borate, bis(glyceryloxyglyceryl) borate, bis{di(glyceryloxy)glyceryl} borate, (glyceryl, xylityl) borate, (glyceryl, sorbityl) borate, (glyceryl, mannityl) borate, (glyceryl, glyceryloxyglyceryl) borate, {glyceryl, di(glyceryloxy)glyceryl} borate, (xylityl, sorbityl) borate, (xylityl, mannityl) borate, (xylityl, glyceryloxyglyceryl) borate, {xylityl, di(glyceryloxy)glyceryl} borate, (sorbityl, mannityl) borate, (sorbityl, glyceryloxyglyceryl) borate, {sorbityl, di(glyceryloxy)glyceryl} borate, (mannityl, glyceryloxyglyceryl) borate, {mannityl, di(glyceryloxy)glyceryl} borate, {glyceryloxyglyceryl, di(glyceryloxy)glyceryl} borate, (ethylene, xylityl) borate, (ethylene, sobityl) borate, (ethylene, mannityl) borate, (ethylene, glyceryloxyglyceryl) borate, {ethylene, di(glyceryloxy)glyceryl} borate, etc.

Further, as the appointed polyhydric alcohols which are the starting material for producing these semipolar borates, there are enumerated ethylene glycol, glycerol, diglycerol, triglycerol, xylitol, sorbitol, mannitol, etc.

The above-mentioned reaction between at least one of the appointed polyhydric alcohols and boric acid can be easily carried out by heating the reaction mixture at a temperature of 50° to 300° C., and preferably 150° to 200° C., under reduced pressure or atmospheric pressure while the water formed is removed out of the reaction system.

The above-mentioned reaction between at least one of the appointed polyhydric alcohols and a lower alkyl triborate can be easily carried out by heating the reaction mixture at a temperature of 30° to 270° C., and preferably 100° to 200° C., under reduced pressure or atmospheric pressure while the alcohol formed is removed out of the reaction system. The lower alkyl triborates used in this case are exemplified by trimethyl borate, triethyl borate, tripropyl borate and triisopropyl borate.

The above-mentioned reaction between at least one of the appointed polyhydric alcohols and boric anhydride can be easily carried out by reacting the starting materials with each other partly at a temperature of 20° to 150° C., and preferably 50° to 90° C. and then heating the reaction mixture at a temperature of 50° to 300° C., and preferably 150° to 250° C., under reduced pressure or atmospheric pressure while the water formed is removed out of the reaction system.

In any one of the said processes, the introduction of an inert gas such as nitrogen gas, carbon dioxide gas, etc. and the use of a solvent such as toluene, xylene, etc. accelerate the reaction.

Here, if bisethylene borate or (ethylene, glyceryl) borate which are beyond the scope of the appointed semipolar borates and which have at most only one hydroxyl group except in their semipolar structure portion is used, the ability of dispersing rubber additives and metals in a brake fluid becomes very weak. Therefore, ethylene glycol must be used in esterification of boric acid in admixture with a polyhydric alcohol having at least four hydroxyl groups.

Also, as the polyhydric alcohols comprising vicinal hydroxyl groups, there can be enumerated 1,2-propylene glycol, 1,2-butylene glycol, etc. in addition to said ethylene glycol. However, these polyhydric alcohols containing an alkyl side chain are not preferable since semipolar borates derived therefrom are remarkably weak in ability of suppressing rubber swelling.

The appointed heteroborates can be prepared by reacting boric acid, a lower alkyl triborate or boric anhydride with a system containing glycol ethers derived from starting alcohols containing butyl group such as ethylene glycol monobutyl ether, diethylene glycol monobutyl ether, triethylene glycol monobutyl ether, etc. and glycol ethers derived from starting alcohols containing methyl group such as triethylene glycol monomethyl ether, tetraethylene glycol monomethyl ether, pentaethylene glycol monomethyl ether, etc. according to a usual process for preparing $SP^2$ type triborates. The heteroborates are exemplified by {mono(monobutoxyethyl), di(monomethoxydiethyleneoxyethyl)} borate, {poly(1.5 moles) (monobutoxyethyl), poly(1.5 moles) (monomethoxydiethyleneoxyethyl)} borate, {mono(monobutoxyethyl), di(monomethoxytriethyleneoxyethyl)} borate, {poly(1.5 moles) (monobutoxyethyl), poly(1.5 moles) (monomethoxytriethyleneoxyethyl)} borate, {mono(monobutoxyethyl), di(monomethoxytetraethyleneoxyethyl)} borate, {poly(1.5 moles) (monobutoxyethyl), poly(1.5 moles) (monomethoxytetraethyleneoxyethyl)} borate, {mono(monobutoxyethyleneoxyethyl), di(monomethoxydiethyleneoxyethyl)} borate, {poly(1.5 moles) (monobutoxyethyleneoxyethyl), poly(1.5 moles) (monomethoxydiethyleneoxyethyl)} borate, {mono(monobutoxyethyleneoxyethyl), di(monomethoxytriethyleneoxyethyl)} borate, {poly(1.5 moles) (monobutoxyethyleneoxyethyl), poly(1.5 moles) (monomethoxytriethyleneoxyethyl)} borate, {mono(monobutoxyethyleneoxyethyl, di(monomethoxytetraethyleneoxyethyl)} borate, {poly(1.5 moles) (monobutoxyethyleneoxyethyl), poly(1.5 moles) (monomethoxytetraethyleneoxyethyl)} borate, {mono(monobutoxydiethyleneoxyethyl), di(monomethoxydiethyleneoxyethyl)} borate, {poly(1.5 moles) (monobutoxydiethyleneoxyethyl), poly(1.5 moles) (monomethoxydiethyleneoxyethyl)} borate, {mono(monobutoxydiethyleneoxyethyl), di(monomethoxytriethyleneoxyethyl)} borate, {poly(1.5 moles) (monobutoxydiethyleneoxyethyl), poly(1.5 moles) (monomethoxytriethyleneoxyethyl)} borate, {mono(monobutoxydiethyleneoxyethyl), di(monomethoxytetraethyleneoxyethyl)} borate, {poly(1.5 moles) (monobutoxydiethyleneoxyethyl), poly(1.5 moles) (monomethoxytetraethyleneoxyethyl)} borate, etc.

If heteroborates containing no butyl group which are beyond the scope of the appointed heteroborates are used, the dissolving power of the ingredients chelated with the appointed semipolar borates is remarkably reduced. Also, if alkyl groups other than methyl group exist together with butyl group in the molecule of the heteroborates, rubber swelling property becomes excessively high and is ill-balanced with the rubber compression properties of the appointed semipolar borates. Therefore, the presence of such alkyl groups is not preferable. Also, it is unsuitable that the amount of the residue of a starting alcohol containing butyl group is larger than the amount of the residue of a starting alcohol containing methyl group, since the dissolving power of the ingredients chelated with the appointed semipolar borates thereby becomes weaker and rubber swelling property is increased.

On the other hand, if the length of an oxyethylene chain in the respective starting alcohols is shorter than that of an oxyethylene chain in the appointed heteroborates, equilibrium reflux point (hereinafter referred to as "ERBP") is reduced. Contrarily, if the former is longer than the latter, the kinetic viscosities of the brake fluids prepared therefrom are remarkably increased. Also, it is not preferable to replace the oxyethylene chain of the appointed heteroborates by another oxyalkylene chain, since it decreases WET-ERBP.

On the other hand, the appointed polyalkylene glycol monoalkyl ethers include not only ethylene oxide adducts such as triethylene glycol monomethyl ether but also ethylene oxide-propylene oxide co-adducts such as monomethoxypropylene glycol tetraethylene glycol ether as represented by the general formula (III). Thus, specific examples of the appointed polyalkylene glycol monoalkyl ethers include triethylene glycol monomethyl ether, tetraethylene glycol monomethyl ether, pentaethyleneglycol monomethyl ether, triethylene glycol monoethyl ether, tetraethylene glycol monoethyl ether, pentaethylene glycol monoethyl ether, triethylene glycol monopropyl ether, tetraethylene glycol monopropyl ether, pentaethylene glycol monopropyl ether, triethylene glycol monoisopropyl ether, tetraethylene glycol monoisopropyl ether, pentaethylene glycol monoisopropyl ether, triethylene glycol monobutyl ether, tetraethylene glycol monobutyl ether, pentaethylene glycol monobutyl ether, monomethoxytriethylene glycol propylene glycol ether, monomethoxytetraethylene glycol propylene glycol ether, monoethoxytriethylene glycol propylene glycol ether, monoethoxytetraethylene glycol propylene glycol ether, monopropoxytriethylene glycol propylene glycol ether, monpropoxytetraethylene glycol propylene glycol ether, monoisopropoxytriethylene glycol propylene glycol ether, monoisopropoxytetraethylene glycol propylene glycol ether, monobutoxytriethylene glycol propylene glycol ether, monobutoxytetraethylene glycol propylene glycol ehter, monomethoxypropylene glycol triethylene glycol ether, monomethoxypropylene glycol tetraethylene glycol ether, monoethoxypropylene glycol triethylene glycol ether, monoethoxypropylene glycol tetraethylene glycol ether, monopropoxypropylene glycol triethylene glycol ether, monpropoxypropylene glycol tetraethylene glycol ether, monoisopropoxypropylene glycol triethylene glycol ether, monoisopropoxypropylene glycol tetraethylene glycol ether, monobutoxypropylene glycol triethylene glycol ether, monobutoxypropylene glycol tetraethylene glycol ether, monomethoxypoly (3.5 moles) ethylene glycol poly(1.5 moles)propylene glycol ether, monoethoxypoly(3.5 moles) ethylene glycol poly(1.5 moles) propylene glycol ether, monpropoxypoly(3.5 moles)ethylene glycol poly(1.5 moles)propylene glycol ether, monoisopropoxypoly(3.5 moles)ethylene glycol poly(1.5 moles)propylene glycol ether, monobutoxypoly(3.5 moles)ethylene glycol poly(1.5 moles)propylene glycol ether, monomethoxypoly(1.5 moles)propylene glycol poly(3.5 moles)ethylene glycol ether, monoethoxypoly(1.5 moles)propylene glycol poly(3.5 moles)ethylene glycol ether, monpropoxypoly(1.5 moles)propylene glycol poly(3.5 moles)ethylene glycol ether, monoisopropoxypoly(1.5 moles)propylene glycol poly(3.5 moles)ethylene glycol ether, monobutoxypoly(1.5 moles)propylene glycol poly(3.5 moles)ethylene glycol ether, etc.

These ethers can be obtained by reacting 3 to 5 moles of ethylene oxide or a mixture of ethylene oxide and propylene oxide (In this case, the amount of ethylene oxide added is 3 moles or more and the amount of propylene oxide added is 1.5 moles or less.) with 1 mole of methyl alcohol, ethyl alcohol, propyl alcohol, ispropyl alcohol or butyl alcohol in the presence or absence of an acid or alkali catalyst at 50° to 300° C. and at 1 to 15 kg/cm$^2$, and preferably at 100° to 150° C. and at 1 to 5 kg/cm$^2$, or by adding 3 moles or more but less than 5 moles of ethylene oxide and then 1.5 moles or less of propylene oxide to 1 mole of the above-mentioned alcohol, or by adding 1.5 moles or less of propylene oxide and then 3 moles or more but less than 5 moles of ethylene oxide to 1 mole of the above-mentioned alcohol.

Here, in a relationship between polyoxyethylene group and polyoxypropylene group in the appointed polyalkylene glycol monoalkyl ether, if the average degree of polymerization of the polyoxyethylene group is lower than 3 as an absolute amount and if the molar fraction of the polyoxypropylene group in polyoxyalkylene group is larger than ⅓, it is impossible to improve the WET-ERBP of a brake fluid obtained by mixing the ether with the appointed semipolar borate and the appointed heteroborate. It is not preferable from the viewpoint of properties.

Also, a pH adjusting agent, a metal corrosion inhibitor and an antioxidant, etc. may be added to the brake fluid composition according to the present invention if necessary. These additives are not limited to specific ones.

As described above, the brake fluid compositions for automobiles according to the present invention can satisfy the second class, No. 2 standard of JIS K-2233 and DOT-4 grade of Federal Motor Vehicles Safety Standard (FMVSS No. 116). Further, they increase WET-ERBP without increasing rubber swelling property and disperse or dissolve homogeneously the additives and metals extracted from rubber cups and cylinder pipes to prevent precipitation thereof. Thus, in rubber swelling property test and metal corrosion test, the brake fluid compositions for automobiles according to the present invention do substantially not show the formation of precipitate in contrast with the brake fluid compositions prepared according to the technique as described in United States Patent specification No. 3,625,899.

The following examples will serve to illustrate the practice of the invention in more detail.

EXAMPLE 1

Into a four-neck flask with a stirrer, a thermometer, a gas inlet and a water measuring tube connected with a reflux condenser were charged 184.2 g. (2 moles) of glycerol and 61.8 g (1 mole) of boric acid. The charged materials were reacted at 190° to 200° C. for 4 hours under nitrogen gas flowing condition. Thus, 54 g of water was distilled off and colorless and transparent bisglyceryl borate was obtained.

Also, into another reactor were charged 118 g (1 mole) of ethylene glycol monobutyl ether, 328 g (2 moles) of triethylene glycol monomethyl ether and 61.8 g (1 mole) of boric acid. The charged materials were reacted at 160° to 170° C. for 3 hours under nitrogen gas flowing condition. Thus, 59 g of water was distilled off and light yellow and transparent {mono(monobutoxyethyl), di(monomethoxydiethyleneoxyethyl)} borate was obtained.

These borates were mixed with triethylene glycol monomethyl ether in the following weight ratio to form a brake fluid composition.

| | % by weight |
|---|---|
| $CH_2O\diagdown{}_{B}\diagup OH_2C$ with CHO, CH$_2$OH, CH$_2$OH branches (bisglyceryl borate structure with $\delta^+H$) | 10 |
| $C_4H_9OCH_2CH_2O\diagdown$<br>$CH_3O-(CH_2CH_2O-)_3-B$<br>$CH_3O-(CH_2CH_2O-)\diagup$ | 9 |
| $CH_3O-(CH_2CH_2O-)_3H$ | 81 |

EXAMPLE 2

Into the same reactor as that used in Example 1 were charged 332.4 g (2 moles) of diglycerol and 145.8 g (1 mole) of triethyl borate. The charged materials were reacted at 90° to 100° C. for 6 hours. Thus, 138 g of ethyl alcohol was distilled off and light yellow and transparent bis(glyceryloxyglyceryl) borate was obtained.

Also, in another reactor, 618 g (3 moles) of triethylene glycol monobutyl ether was first reacted with 69.6 g (1 mole) of boric anhydride at 80° to 90° C. Then, 756 g (3 moles) of pentaethylene glycol monomethyl ether was charged and the mixture was reacted at 190° to 200° C. Thus, 54 g of water was distilled off and colorless and transparent {poly(1.5 moles)(monobutoxydiethyleneoxyethyl), poly(1.5 moles)(monomethoxytetraethyleneoxyethyl)} borate was obtained. These borates were mixed with tetraethylene glycol monoethyl ether in the following weight ratio to form a brake fluid composition.

| | % by weight |
|---|---|
| Bis(glyceryloxyglyceryl) borate structure with $CH_2O$, CHO, $CH_2$, O, $CH_2$, CHOH, $CH_2OH$ branches on both sides of B ($\delta^+H$) | 1 |
| $[\{C_4H_9O-(CH_2CH_2O-)_{\overline{3}}\}_{1.5} \cdot \{CH_3O-(CH_2CH_2O-)_{\overline{5}}\}_{1.5}]B$ | 29 |
| $C_2H_5O-(CH_2CH_2O-)_4H$ | 70 |

EXAMPLE 3

In the same manner as in Example 1, 92.1 g (1 mole) of glycerol, 260 g (corresponding to 1 mole) of a 70% aqueous sorbitol and 61.8 g (1 mole) of boric acid were reacted to obtain (glyceryl, sorbityl) borate which was light yellow and transparent liquid.

Also, 162 g (1 mole) of diethylene glycol monobutyl ether, 416 g (2 moles) of tetraethylene glycol monomethyl ether and 188.1 g (1 mole) of triisopropyl borate were reacted to obtain {mono(monobutoxyethyleneoxyethyl), di(monomethoxytriethyleneoxyethyl)} borate.

These borates were mixed with monomethoxytriethylene glycol propylene glycol ether in the following weight ratio to form a brake fluid composition.

| | % by weight |
|---|---|
| (Glyceryl, sorbityl) borate structure with CHO, CHOH, HOCH, CHOH, $CH_2OH$ and $CH_2OH$ branches on B ($\delta^+H$) | 1 |
| $C_4H_9O-(CH_2CH_2O-)_2\diagdown$<br>$CH_3O-(CH_2CH_2O-)_4-B$<br>$CH_3O-(CH_2CH_2O-)_4\diagup$ | 25 |
| $CH_3O-(CH_2CH_2O-)_3-\overset{\underset{\displaystyle CH_3}{\mid}}{C}HCH_2OH$ | 74 |

EXAMPLE 4

Borates and a polyalkylene glycol monoalkyl ether were mixed in the following weight ratio to form a brake fluid composition.

| | % by weight |
|---|---|
| 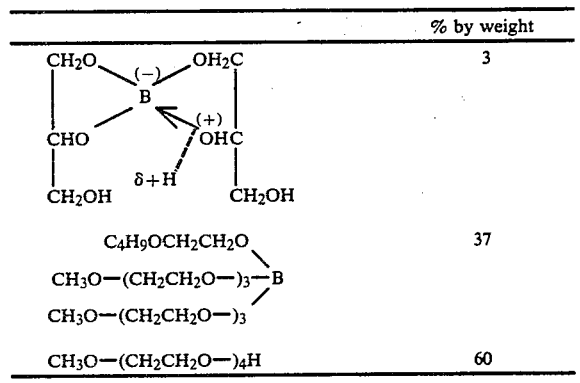 | 3 |
| | 37 |
| $CH_3O-(CH_2CH_2O-)_4H$ | 60 |

EXAMPLE 5

Borates and a polyalkylene glycol monoalkyl ether were mixed in the following weight ratio to form a brake fluid composition.

| | % by weight |
|---|---|
| 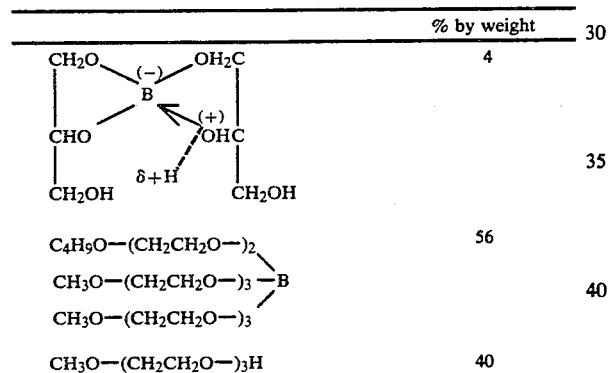 | 4 |
| | 56 |
| $CH_3O-(CH_2CH_2O-)_3H$ | 40 |

EXAMPLE 6

Borates and a polyalkylene glycol monoalkyl ether were mixed in the following weight ratio to form a brake fluid composition.

| | % by weight |
|---|---|
| 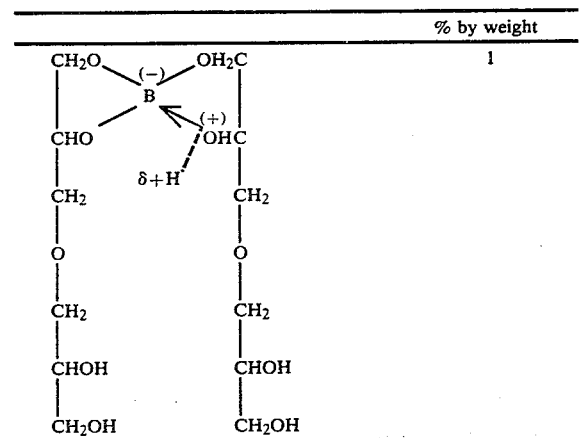 | 1 |

| | % by weight |
|---|---|
| | 49 |
| $CH_3O-(CH_2CH_2O-)_3H$ | 50 |

EXAMPLE 7

Borates and a polyalkylene glycol monoalkyl ether were mixed in the following weight ratio to form a brake fluid composition.

| | % by weight |
|---|---|
| 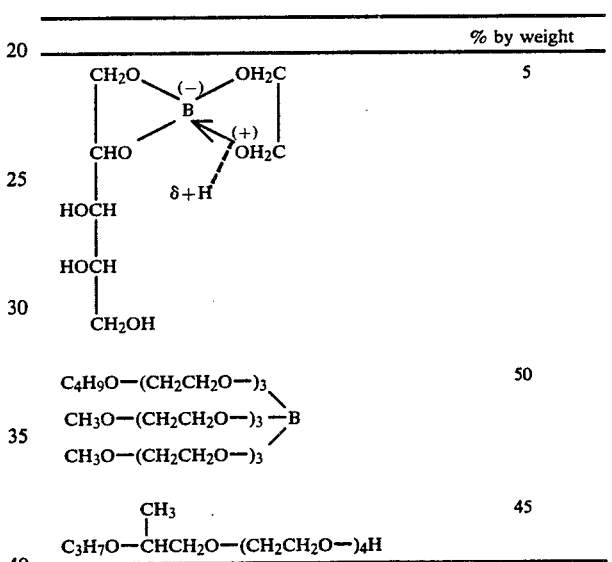 | 5 |
| | 50 |
| $C_3H_7O-\overset{CH_3}{\underset{|}{C}H}CH_2O-(CH_2CH_2O-)_4H$ | 45 |

EXAMPLE 8

Borates and a polyalkylene glycol monoalkyl ehter were mixed in the following weight ratio to form a brake fluid composition.

| | % by weight |
|---|---|
| 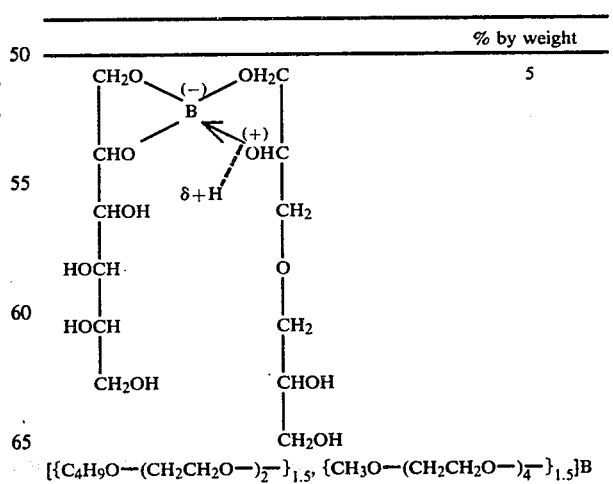 | 5 |
| $[\{C_4H_9O-(CH_2CH_2O-)_{\overline{2}}\}_{1.5}, \{CH_3O-(CH_2CH_2O-)_{\overline{4}}\}_{1.5}]B$ | 30 |

-continued

| | % by weight |
|---|---|
| $\begin{array}{c}CH_3\phantom{xxx}CH_3\\ \phantom{xx}\backslash\phantom{xxxx}|\\ CHO-CHCH_2O-(CH_2CH_2O-)_3H\\ /\\ CH_3\end{array}$ | 65 |

EXAMPLE 9

Borates and a polyalkylene glycol monoalkyl ether were mixed in the following weight ratio to form a brake fluid composition.

| | % by weight |
|---|---|
| [structure with B center, CH₂O/OH₂C groups, CHO/OHC, CH₂OH, and side chain with CH₂-O-CH₂-CHOH-CH₂OH] $[\{C_4H_9O-(CH_2CH_2O-)_{\overline{3}}\}_{1.5}, \{CH_3O-(CH_2CH_2O-)_{\overline{3}}\}_{1.5}]B$ | 3 |
| | 50 |
| $C_2H_5O-(CH_2CH_2O-)_5H$ | 47 |

EXAMPLE 10

Borates and a polyalkylene glycol monoalkyl ether were mixed in the following weight ratio to form a brake fluid composition.

| | % by weight |
|---|---|
| [borate structure with CH₂O/OH₂C, CHO/OHC, HOCH/CHOH, HOCH/CHOH, CH₂OH/HOCH₂] | 2 |
| $\begin{array}{c}C_4H_9O-CH_2CH_2O\\ \phantom{xxxxxx}\backslash\\ CH_3O-(CH_2CH_2O-)_4-B\\ \phantom{xxxxxx}/\\ CH_3O-(CH_2CH_2O-)_4\end{array}$ | 48 |
| $C_3H_7O-(CH_2CH_2O-)_3H$ | 50 |

EXAMPLE 11

Borates and a polyalkylene glycol monoalkyl ether were mixed in the following weight ratio to form a brake fluid composition.

| | % by weight |
|---|---|
| [borate structure with CH₂O/OH₂C, CHO/OHC, CHOH/CHOH, HOCH/CHOH, HOCH/HOCH₂, CH₂OH] | 6 |
| $\begin{array}{c}C_4H_9O-(CH_2CH_2O-)_2\\ \phantom{xxxxxx}\backslash\\ CH_3O-(CH_2CH_2O-)_3-B\\ \phantom{xxxxxx}/\\ CH_3O-(CH_2CH_2O-)_3\end{array}$ | 44 |
| $C_2H_5O-(CH_2CH_2O-)_3H$ | 50 |

EXAMPLE 12

Borates and a polyalkylene glycol monoalkyl ether were mixed in the following weight ratio to form a brake fluid composition.

| | % by weight |
|---|---|
| [borate structure with CH₂O/OH₂C, CHO/OH₂C, CH₂, O, CH₂, CHOH, CH₂OH side chain] $[\{C_4H_9O-(CH_2CH_2O-)_{\overline{3}}\}_{1.5}, \{CH_3O-(CH_2CH_2-)_{\overline{3}}\}_{1.5}]B$ | 1 |
| | 9 |
| $\begin{array}{c}CH_3\\ |\\ CH_3O-CHCH_2O-(CH_2CH_2O-)_3H\end{array}$ | 90 |

EXAMPLE 13

Borates and a polyalkylene glycol monoalkyl ether were mixed in the following weight ratio to form a brake fluid composition.

| | % by weight |
|---|---|
| $\begin{array}{c} CH_2O \diagdown \diagup OH_2C \\ \phantom{CH_2O}{}^{(-)}\!B \\ CHO \diagup \phantom{B}\diagdown {}^{(+)}\!\!OHC \\ \phantom{CHO\diagup}\delta+H \\ CH_2 \phantom{XXX} CH_2 \\ | \phantom{XXX} | \\ O \phantom{XXXXX} O \\ | \phantom{XXX} | \\ CH_2 \phantom{XXX} CH_2 \\ | \phantom{XXX} | \\ CHOH \phantom{XX} CHOH \\ | \phantom{XXX} | \\ CH_2OH \phantom{X} CH_2OH \end{array}$ | 3 |
| $\begin{array}{c} C_4H_9O-CH_2CH_2O \diagdown \\ CH_3O-(CH_2CH_2O-)_3-B \\ CH_3O-(CH_2CH_2O-)_3 \diagup \end{array}$ | 52 |
| $CH_3O-(CH_2CH_2O-)_{3.5}-\left(\begin{array}{c} CH_3 \\ | \\ CHCH_2O- \end{array}\right)_{1.5}\!\!H$ | 45 |

EXAMPLE 14

Borates and a polyalkylene glycol monoalkyl ether were mixed in the following weight ratio to form a brake fluid composition.

| | % by weight |
|---|---|
| $\begin{array}{c} CH_2O \diagdown \diagup OH_2C \\ \phantom{CH_2O}{}^{(-)}\!B \\ CH \diagup \phantom{B}\diagdown {}^{(-)}\!\!OHC \\ \phantom{CH\diagup}\delta+H \phantom{XXX} CH_2OH \\ CHOH \\ | \\ HOCH \\ | \\ CHOH \\ | \\ CH_2OH \end{array}$ | 1 |
| $[(C_4H_9O-CH_2CH_2O-)_{1.5}, \{(CH_3O-(CH_2CH_2O-)_3-\}_{1.5}]B$ | 50 |
| $C_2H_5O-\left(\begin{array}{c} CH_3 \\ | \\ CHCH_2O- \end{array}\right)_{1.5}\!\!-(CH_2CH_2O-)_{3.5}H$ | 49 |

EXAMPLE 15

Borates and a polyalkylene glycol monoalkyl ether were mixed in the following weight ratio to form a brake fluid composition.

| | % by weight |
|---|---|
| $\begin{array}{c} CH_2O \diagdown \diagup OH_2C \\ \phantom{CH_2O}{}^{(-)}\!B \\ CHO \diagup \phantom{B}\diagdown {}^{(+)}\!\!OHC \\ \phantom{CHO\diagup}\delta+H \phantom{XXX} CH_2OH \\ HOCH \\ | \\ HOCH \\ | \\ CH_2OH \end{array}$ | 10 |
| $[(C_4H_9O-CH_2CH_2O-)_{1.5}, \{CH_3O-(CH_2CH_2O-)_{1.5}]B$ | 50 |
| $CH_3O-(CH_2CH_2O-)_3H$ | 40 |

EXAMPLE 16

Borates and polyalkylene glycol monoalkyl ethers were mixed in the following weight ratio to form a brake fluid composition.

| | % by weight |
|---|---|
| $\begin{array}{c} CH_2O \diagdown \diagup OH_2C \\ \phantom{CH_2O}{}^{(-)}\!B \\ CHO \diagup \phantom{B}\diagdown {}^{(+)}\!\!OHC \\ \phantom{CHO\diagup}\delta+H \\ CH_2OH \phantom{XX} CH_2OH \end{array}$ | 3 |
| $\begin{array}{c} C_4H_9O-CH_2CH_2O \diagdown \\ CH_3O-(CH_2CH_2O-)_3-B \\ CH_3O-(CH_2CH_2O-)_3 \diagup \end{array}$ | 27 |
| $C_4H_9O-(CH_2CH_2O)_5H$ | 10 |
| $CH_3O-(CH_2CH_2O-)_4H$ | 60 |

EXAMPLE 17

Borates and polyalkylene glycol monoalkyl ethers were mixed in the following weight ratio to form a brake fluid composition.

| | % by weight |
|---|---|
| $\begin{array}{c} CH_2O \diagdown \diagup OH_2C \\ \phantom{CH_2O}{}^{(-)}\!B \\ CHO \diagup \phantom{B}\diagdown {}^{(+)}\!\!OHC \\ \phantom{CHO\diagup}\delta+H \\ CH_2OH \phantom{XX} CH_2OH \end{array}$ | 5 |
| $[\{C_4H_9O-(CH_2CH_2O-)_2-\}_{1.5}, \{CH_3O-(CH_2CH_2O-)_4-\}_{1.5}]B$ | 25 |
| $\begin{array}{c} CH_3 \diagdown \phantom{XXXXXXXXXX} CH_3 \\ \phantom{CH_3}CHO-(CH_2CH_2O-)_4-CHCH_2OH \\ CH_3 \diagup \end{array}$ | 20 |
| $C_2H_5O-(CH_2CH_2-O)_3H$ | 50 |

EXAMPLE 18

Borates and polyalkylene glycol monoalkyl ethers were mixed in the following weight ratio to form a brake fluid composition.

|  | % by weight |
|---|---|
| $\begin{array}{c}\text{CH}_2\text{O}\diagdown\underset{\text{B}}{(-)}\diagup\text{OH}_2\text{C}\\\text{CHO}\qquad\overset{(+)}{\longleftarrow}\text{OHC}\\\quad\delta+\text{H}\\\text{CHOH}\qquad\text{HOCH}\\\text{HOCH}\qquad\text{CHOH}\\\text{CHOH}\qquad\text{HOCH}\\\text{CH}_2\text{OH}\qquad\text{HOCH}_2\end{array}$ | 3 |
| $\begin{array}{c}\text{C}_4\text{H}_9\text{O}-\text{CH}_2\text{CH}_2\text{O}\diagdown\\\text{CH}_3\text{O}-(\text{CH}_2\text{CH}_2\text{O}-)_3-\text{B}\\\text{CH}_3\text{O}-(\text{CH}_2\text{CH}_2\text{O}-)_3\diagup\end{array}$ | 27 |
| $\text{CH}_3\text{O}-\left(\begin{array}{c}\text{CH}_3\\|\\\text{CHCH}_2\text{O}-\end{array}\right)_{1.5}(\text{CH}_2\text{CH}_2\text{O}-)_{3.5}\text{H}$ | 30 |
| $\text{CH}_3\text{O}-(\text{CH}_2\text{CH}_2\text{O}-)_3\text{H}$ | 40 |

EXAMPLE 19

Borates and polyalkylene glycol monoalkyl ethers were mixed in the following weight ratio to form a brake fluid composition.

|  | % by weight |
|---|---|
| $\begin{array}{c}\text{CH}_2\text{O}\diagdown\underset{\text{B}}{(-)}\diagup\text{OH}_2\text{C}\\\text{CHO}\qquad\overset{(+)}{\longleftarrow}\text{OHC}\\\quad\delta+\text{H}\\\text{HOCH}\qquad\text{CH}_2\text{OH}\\\text{HOCH}\\\text{CH}_2\text{OH}\end{array}$ | 5 |
| $[\{\text{C}_4\text{H}_9\text{O}-(\text{CH}_2\text{CH}_2\text{O}-)_3-\}_{1.5},\{\text{CH}_3\text{O}-(\text{CH}_2\text{CH}_{20}-)_5-\}_{1.5}]\text{B}$ | 15 |
| $\text{C}_4\text{H}_9\text{O}-(\text{CH}_2\text{CH}_2\text{O}-)_3\text{H}$ | 15 |
| $\text{C}_2\text{H}_5\text{O}-(\text{CH}_2\text{CH}_2\text{O}-)_4\text{H}$ | 65 |

EXAMPLE 20

Borates and polyalkylene glycol monoalkyl ethers were mixed in the following weight ratio to form a brake fluid composition.

|  | % by weight |
|---|---|
| $\begin{array}{c}\text{CH}_2\text{O}\diagdown\underset{\text{B}}{(-)}\diagup\text{OH}_2\text{C}\\\text{CHO}\qquad\overset{(+)}{\longleftarrow}\text{OH}_2\text{C}\\\quad\delta+\text{H}\\\text{CH}_2\\|\\\text{O}\\|\\\text{CH}_2\\|\\\text{CHOH}\\|\\\text{CH}_2\text{OH}\end{array}$ | 2 |
| $\begin{array}{c}\text{C}_4\text{H}_9\text{O}-(\text{CH}_2\text{CH}_2\text{O}-)_2\diagdown\\\text{CH}_3\text{O}-(\text{CH}_2\text{CH}_2\text{O}-)_4-\text{B}\\\text{CH}_3\text{O}-(\text{CH}_2\text{CH}_2\text{O}-)_4\diagup\end{array}$ | 10 |
| $\begin{array}{c}\text{CH}_3\\|\\\text{C}_2\text{H}_5\text{O}-(\text{CH}_2\text{CH}_2\text{O}-)_3-\text{CHCH}_2\text{OH}\end{array}$ | 38 |
| $\text{C}_2\text{H}_5\text{O}-(\text{CH}_2\text{CH}_2\text{O}-)_4\text{H}$ | 50 |

EXAMPLE 21

Borates and polyalkylene glycol monoalkyl ethers were mixed in the following weight ratio to form a brake fluid composition.

|  | % by weight |
|---|---|
| $\begin{array}{c}\text{CH}_2\text{O}\diagdown\underset{\text{B}}{(-)}\diagup\text{OH}_2\text{C}\\\text{CHO}\qquad\overset{(+)}{\longleftarrow}\text{OH}_2\text{C}\\\quad\delta+\text{H}\\\text{HOCH}\\|\\\text{HOCH}\\|\\\text{CH}_2\text{OH}\end{array}$ | 3 |
| $[(\text{C}_4\text{H}_9\text{O}-\text{CH}_2\text{CH}_2\text{O}-)_{1.5},\{\text{CH}_3\text{O}-(\text{CH}_2\text{CH}_2\text{O}-)_3-\}_{1.5}]\text{B}$ | 47 |
| $\text{CH}_3\text{O}-\left(\begin{array}{c}\text{CH}_3\\|\\\text{CHCH}_2\text{O}-\end{array}\right)_{1.5}-(\text{CH}_2\text{CH}_2\text{O}-)_{3.5}\text{H}$ | 25 |
| $\text{CH}_3\text{O}-(\text{CH}_2\text{CH}_2\text{O}-)_{3.5}-\left(\begin{array}{c}\text{CH}_3\\|\\\text{CHCH}_2\text{O}-\end{array}\right)_{1.5}\text{H}$ | 25 |

EXAMPLE 22

Borates and a polyalkylene glycol monoalkyl ether were mixed in the following weight ratio to form a brake fluid composition.

|  | % by weight |
|---|---|
| $\begin{array}{c}\text{CH}_2\text{O}\diagdown\underset{\text{B}}{(-)}\diagup\text{OH}_2\text{C}\\\text{CHO}\qquad\overset{(+)}{\longleftarrow}\text{OHC}\\\quad\delta+\text{H}\\\text{CH}_2\text{OH}\qquad\text{CH}_2\text{OH}\end{array}$ | 3 |
| $\begin{array}{c}\text{C}_4\text{H}_9\text{OCH}_2\text{CH}_2\text{O}\diagdown\\\text{CH}_3\text{O}-(\text{CH}_2\text{CH}_2\text{O}-)_4-\text{B}\\\text{CH}_3\text{O}-(\text{CH}_2\text{CH}_2\text{O}-)_4\diagup\end{array}$ | 15 |
| $\begin{array}{c}\text{C}_4\text{H}_9\text{O}-(\text{CH}_2\text{CH}_2\text{O}-)_2\diagdown\\\text{CH}_3\text{O}-(\text{CH}_2\text{CH}_2\text{O}-)_3-\text{B}\\\text{CH}_3\text{O}-(\text{CH}_2\text{CH}_2\text{O}-)_3\diagup\end{array}$ | 15 |
| $\text{CH}_3\text{O}-(\text{CH}_2\text{CH}_2\text{O}-)_4\text{H}$ | 67 |

EXAMPLE 23

Borates and a polyalkylene glycol monoalkyl ether were mixed in the following weight ratio to form a brake fluid composition.

|  | % by weight |
|---|---|
| CH₂O−B(−)−OH₂C with CHO, CH₂OH / OHC(+), CH₂OH, δ+H | 1 |
| C₄H₉O−CH₂CH₂−O \ CH₃O−(CH₂CH₂O−)₃ − B / CH₃O−(CH₂CH₂O−)₃ | 45 |
| [{C₄H₉O−(CH₂CH₂O−)₃−}₁.₅, {CH₃O−(CH₂CH₂O−)₅−}₁.₅]B | 5 |
| C₂H₅O−(CH₂CH₂O−)₃.₅−(CH(CH₃)CH₂O−)₁.₅H | 49 |

EXAMPLE 24

Borates and a polyalkylene glycol monoalkyl ether were mixed in the following weight ratio to form a brake fluid composition.

|  | % by weight |
|---|---|
| CH₂O−B(−)−OH₂C with CHO, CH₂, O, CH₂, CHOH, CH₂OH / OHC(+), CH₂, O, CH₂, CHOH, CH₂OH, δ+H | 4 |
| [(C₄H₉OCH₂CH₂O−)₁.₅, {CH₃O−(CH₂CH₂O−)₅−}₁.₅]B | 10 |
| [{C₄H₉O−(CH₂CH₂O−)₂−}₁.₅, {CH₃O−(CH₂CH₂O−)₃−}₁.₅]B | 36 |
| C₃H₇O−(CH₂CH₂O−)₃H | 50 |

EXAMPLE 25

Borates and a polyalkylene glycol monoalkyl ether were mixed in the following weight ratio to form a brake fluid composition

|  | % by weight |
|---|---|
| CH₂O−B(−)−OH₂C with CHO, CHOH, HOCH, CHOH, CH₂OH / OHC(+), CHOH, HOCH, CHOH, CH₂OH, δ+H | 2 |
| CH₂O−B(−)−OH₂C with CHO, CH₂OH / OHC(+), CH₂OH, δ+H | 2 |

|  | % by weight |
|---|---|
| C₄H₉O−CH₂CH₂O \ CH₃O−(CH₂CH₂O−)₄ − B / CH₃O−(CH₂CH₂O−)₄ | 46 |
| CH₃ \ CHO−(CH₂CH₂O−)₃H / CH₃ | 50 |

EXAMPLE 26

Borates and polyalkylene glycol monoalkyl ethers were mixed in the following weight ratio to form a brake fluid composition.

|  | % by weight |
|---|---|
| CH₂O−B(−)−OH₂C with CHO, CHOH, HOCH, CHOH, CH₂OH / OHC(+), CH₂OH, δ+H | 2 |
| CH₂O−B(−)−OH₂C with CHO, CH₂OH / OHC(+), CH₂OH, δ+H | 3 |
| [(C₄H₉O−CH₂CH₂O−)₁.₅, {CH₃O−(CH₂CH₂O−)₃−}₁.₅]B | 25 |
| C₄H₉O−(CH₂CH₂O−)₃.₅−(CH(CH₃)CH₂O−)₁.₅H | 10 |
| CH₃O−(CH₂CH₂O−)₃H | 60 |

EXAMPLE 27

Borates and a polyalkylene glycol monoalkyl ether were mixed in the following weight ratio to form a brake fluid composition.

|  | % by weight |
|---|---|
| CH₂O−B(−)−OH₂C with CHO, CH₂, O, CH₂, CHOH, CH₂OH / OHC(+), CH₂, O, CH₂, CHOH, CH₂OH, δ+H | 1 |

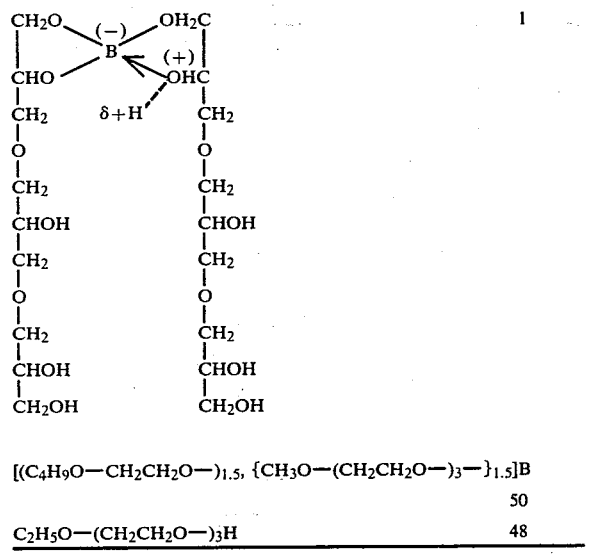

| | % by weight |
|---|---|
| [(C₄H₉O—CH₂CH₂O—)₁.₅, {CH₃O—(CH₂CH₂O—)₃—}₁.₅]B | 50 |
| C₂H₅O—(CH₂CH₂O—)₃H | 48 |

EXAMPLE 28

Borates and a polyalkylene glycol monoalkyl ether were mixed in the following weight ratio to form a brake fluid composition.

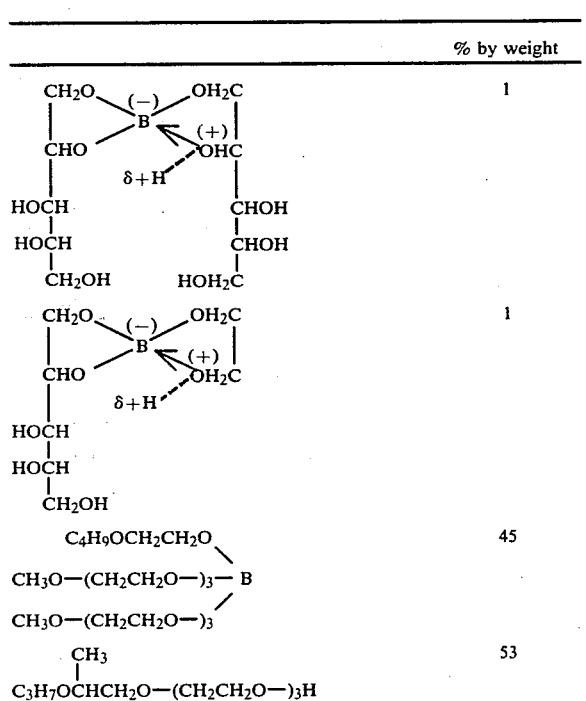

| | % by weight |
|---|---|
| (structure 1) | 1 |
| (structure 2) | 1 |
| C₄H₉OCH₂CH₂O\ CH₃O—(CH₂CH₂O—)₃—B / CH₃O—(CH₂CH₂O—)₃ | 45 |
| CH₃ \| C₃H₇OCHCH₂O—(CH₂CH₂O—)₃H | 53 |

EXAMPLE 29

Borates and polyalkylene glycol monoalkyl ethers were mixed in the following weight ratio to form a brake fluid composition.

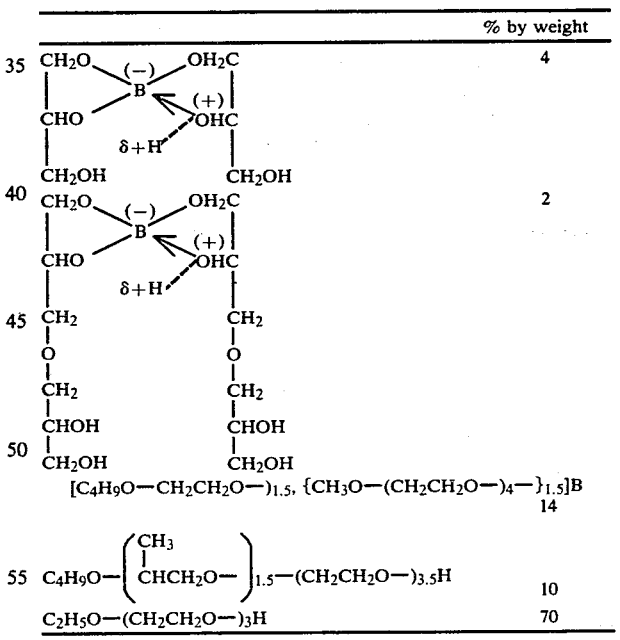

| | % by weight |
|---|---|
| (borate structure) | 10 |
| C₄H₉OCH₂CH₂O\ CH₃O—(CH₂CH₂O—)₃—B / CH₃O—(CH₂CH₂O—)₃ | 6 |
| C₄H₉O—CH₂CH₂O—)₂\ CH₃O—(CH₂CH₂O—)₃—B / CH₃O—(CH₂CH₂O—)₃ | 3 |
| C₃H₇O—(CH₂CH₂CH₂O—)₃.₅—(CH₃\|CHCH₂O—)₁.₅H | 11 |
| C₂H₅O—(CH₂CH₂O—)₃H | 70 |

EXAMPLE 30

Borates and polyalkylene glycol monoalkyl ethers were mixed in the following weight ratio to form a brake fluid composition.

| | % by weight |
|---|---|
| (borate structure 1) | 4 |
| (borate structure 2) | 2 |
| [C₄H₉O—CH₂CH₂O—)₁.₅, {CH₃O—(CH₂CH₂O—)₄—}₁.₅]B | 14 |
| C₄H₉O—(CH₃\|CHCH₂O—)₁.₅—(CH₂CH₂O—)₃.₅H | 10 |
| C₂H₅O—(CH₂CH₂O—)₃H | 70 |

COMPARATIVE EXAMPLE 1

According to U.S. Pat. No. 3,625,899, 65% by weight of tris(monomethoxydiethyleneoxyethyl) borate and 35% by weight of triethylene glycol monomethyl ether were mixed to form a brake fluid composition.

COMPARATIVE EXAMPLE 2

According to U.S. Pat. No. 3,625,899, 55% by weight of tris(monobutoxydiethyleneoxyethyl) borate and 45% by weight of triethylene glycol monomethyl ether were mixed to form a brake fluid composition.

COMPARATIVE EXAMPLE 3

According to U.S. Pat. No. 3,625,899, 70% by weight of {mono(monobutoxyethyleneoxyethyl), di(monodiethyleneoxyethyl)} borate and 30% by weight of triethylene glycol monomethyl ether were mixed to form a brake fluid composition.

COMPARATIVE EXAMPLE 4

According to U.S. Pat. No. 3,625,899, 75% by weight of {poly(1.5 moles) (monobutoxyethyleneoxyethyl), poly(1.5 moles) (monomethoxydiethyleneoxyethyl)} borate and 25% by weight of triethylene glycol monomethyl ether were mixed to form a brake fluid composition.

The physical properties values of the products of Examples 1 to 30 and Comparative Examples 1 to 4 as well as a commercially brake fluid composition comprising triethylene glycol monomethyl ether are shown in the following table in comparison with the second class, No. 2 standard of JIS K-2233 (Motor Vehicle Brake Fluids) and DOT-4 grade of Federal Motor Vehicles Safety Standard (FMVSS No. 116).

Table

| Test item Example No. | ERBP (°C.) (760mmHg) | WET-ERBP (°C.) (760 mmHg) | Kinetic viscosity at −40° C. (cst) | Rubber swelling property (120 ± 2° C., 70 ± 2 hour treatment) | Volume* of precipitate (cc) (for 75cc of test fluid) | Weight of** precipitate (mg) (for 75cc of test fluid) |
|---|---|---|---|---|---|---|
| JIS K-2233 2nd class No. 2 | 190 or more | | 1800 or less | Change in base diameter of SBR test cup 0.15–1.4mm | | |
| FMVSS DOT-4 grade | 230 or more | 155 or more | 1800 or less | Change in base diameter of SBR test cup 0.15–1.4mm | | |
| Example 1 | 260 | 170 | 1326 | Change in base diameter of cup 0.15 mm | 0 | 0 |
| Example 2 | 269.5 | 167 | 1612 | Change in base diameter of cup 0.20 mm | 0.08 | 16 |
| Example 3 | 266 | 167 | 1590 | Change in base diameter of cup 0.35 mm | 0.08 | 19 |
| Example 4 | 265 | 179 | 1595 | Change in base diameter of cup 0.25 mm | 0.05 | 5 |
| Example 5 | 273 | 183 | 1705 | Change in base diameter of cup 0.25 mm | 0 | 0 |
| Example 6 | 260.5 | 174.5 | 1197 | Change in base diameter of cup 0.35 mm | 0.08 | 15 |
| Example 7 | 279 | 185 | 1792 | Change in base diameter of cup 0.35 mm | 0.03 | 7 |
| Example 8 | 263 | 179 | 1705 | Change in base diameter of cup 0.35 mm | 0.04 | 9 |
| Example 9 | 279.5 | 182 | 1778 | Change in base diameter of cup 0.20 mm | 0 | 0 |
| Example 10 | 270 | 180 | 1358 | Change in base diameter of cup 0.20 mm | 0.04 | 11 |
| Example 11 | 264 | 185 | 1715 | Change in base diameter of cup 0.15 mm | 0 | 0 |
| Example 12 | 261 | 159 | 1297 | Change in base diameter of cup 0.20 mm | 0.06 | 12 |
| Example 13 | 276 | 180.5 | 1788 | Change in base diameter of cup 0.35 mm | 0.02 | 4 |
| Example 14 | 272 | 179 | 1702 | Change in base diameter of cup 0.40 mm | 0.09 | 13 |
| Example 15 | 265 | 183 | 1790 | Change in base diameter of cup 0.15 mm | 0 | 0 |
| Example 16 | 263 | 174 | 1405 | Change in base diameter of cup 0.15 mm | 0 | 0 |
| Example 17 | 270 | 179 | 1730 | Change in base diameter of cup 0.20 mm Change in base | 0 | 0 |

Table-continued

| Example No. | ERBP (°C.) (760mmHg) | WET-ERBP (°C.) (760 mmHg) | Kinetic viscosity at −40° C. (cst) | Rubber swelling property (120 ± 2° C., 70 ± 2 hour treatment) | Volume* of precipitate (cc) (for 75cc of test fluid) | Weight of** precipitate (mg) (for 75cc of test fluid) |
|---|---|---|---|---|---|---|
| Example 18 | 268.5 | 173 | 1755 | Change in base diameter of cup 0.20 mm | 0.01 | 2 |
| Example 19 | 269.5 | 169 | 1610 | Change in base diameter of cup 0.25 mm | 0 | 0 |
| Example 20 | 268.5 | 159 | 1592 | Change in base diameter of cup 0.25 mm | 0.03 | 8 |
| Example 21 | 272 | 180 | 1787 | Change in base diameter of cup 0.40 mm | 0.06 | 13 |
| Example 22 | 267 | 178 | 1565 | Change in base diameter of cup 0.25 mm | 0 | 0 |
| Example 23 | 270.5 | 177.5 | 1716 | Change in base diameter of cup 0.40 mm | 0.09 | 20 |
| Example 24 | 268 | 181 | 1710 | Change in base diameter of cup 0.30 mm | 0.02 | 5 |
| Example 25 | 270 | 183 | 1721 | Change in base diameter of cup 0.30 mm | 0 | 0 |
| Example 26 | 262 | 175 | 1580 | Change in base diameter of cup 0.20 mm | 0.02 | 4 |
| Example 27 | 260 | 170 | 1289 | Change in base diameter of cup 0.35 mm | 0.08 | 19 |
| Example 28 | 267.5 | 170 | 1415 | Change in base diameter of cup 0.40 mm | 0.08 | 20 |
| Example 29 | 274 | 169.5 | 1790 | Change in base diameter of cup 0.15 mm | 0 | 0 |
| Example 30 | 261 | 168 | 1350 | Change in base diameter of cup 0.15 mm | 0 | 0 |
| Commercially available product*** | 249 | 147 | 252 | Change in base diameter of cup 0.20 mm | 0.3 | 89 |
| Comparative Example 1 | 278 | 170 | 1998 | Change in base diameter of cup 0.55 mm | 0.65 | 118 |
| Comparative Example 2 | 277 | 155 | 2087 | Change in base diameter of cup 1.80 mm | 1.40 | 248 |
| Comparative Example 3 | 271 | 168 | 2009 | Change in base diameter of cup 1.75 mm | 1.20 | 203 |
| Comparative Example 4 | 269.5 | 161 | 2015 | Change in base diameter of cup 1.90 mm | 1.35 | 211 |

Notes:
*Volume of precipitate was measured by charging 75 ml of a brake fluid after rubber swelling property test into the test tube as described om JIS K-2504 (Lubricating Oil Precipitation Number Testing Method) and then centrifuging at 2000 rpm for 30 minutes.
**Weight of precipitate was measured by dispersing the precipitate obtained by said centrifugation in 75 ml of ethyl alcohol to wash the precipitate, repeating the washing operation, and then drying the precipitate at 70±2° C., for 15 hours to remove ethanol.
***Trisethylene glycol monomethyl ether.

what is claimed is:

1. A brake fluid composition for automobiles comprising a mixture of 1–10% by weight of at least one semipolar borate represented by the general formula,

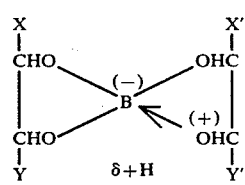

wherein X, X', Y and Y' each are hydrogen atom, a group of the formula,

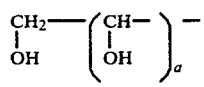

wherein a is 0, 1, 2 or 3, or a group of the formula,

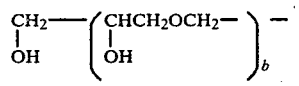

wherein b is 1 or 2 provided that at least two hydroxyl groups are present in X+X'+Y+Y'; 9–50% by weight of at least one heteroborate represented by the general formula,

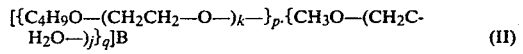

wherein p is a positive number of 1 to 3/2, q is a positive number of 3/2 to 2 and p+q is 3, k is a positive number of 1 to 3, and j is a positive number of 3 to 5; and 40–90% by weight of at least one polyalkylene glycol monoalkyl ether represented by the general formula,

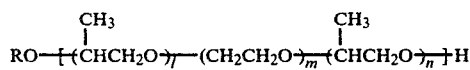

wherein R is a $C_1$–$C_4$ alkyl, l is 0 or a positive number of 3/2 or less, n is 0 or a positive number or 3/2 or less, and m is a positive number of 3 to 5 provided that there are the following relationships between l, m and n;

$$3 \leq (l+m+n) \leq 5$$

and $$0 \leq l+n/(l+m+n) \leq \tfrac{1}{3}.$$

2. A brake fluid composition for automobiles according to claim 1, wherein said mixture as an effective ingredient is a mixture of bisglyceryl borate, {mono(-monobutoxyethyl), di(monomethoxydiethyleneoxyethyl)}borate and triethylene glycol monomethyl ether.

3. A brake fluid composition for automobiles according to claim 1, wherein said mixture is a mixture of bisglyceryl borate, {mono(monobutoxyethyl), di(-monomethoxydiethyleneoxyethyl)} borate and tetraethylene glycol monomethyl ether.

4. A brake fluid composition for automobiles according to claim 1, wherein said mixture is a mixture of bisglyceryl borate, {mono(monobutoxyethyleneoxyethyl), di(monomethoxydiethyleneoxyethyl)} borate and triethylene glycol monomethyl ether.

5. A brake fluid composition for automobiles according to claim 1, wherein said mixture is a mixture of bis(glyceryloxyglyceryl) borate, {mono(monobutoxyethyl), di(monomethoxydiethyleneoxyethyl)} borate and triethylene glycol monomethyl ether.

6. A brake fluid composition for automobiles according to claim 1, wherein said mixture is a mixture of bisglyceryl borate, {mono(monobutoxyethyl), di(-monomethoxytriethyleneoxyethyl)} borate, {mono(-monobutoxyethyleneoxyethyl), di(monomethoxydiethyleneoxyethyl)} borate and tetraethylene glycol monomethyl ether.

7. A brake fluid composition for automobiles according to claim 1, wherein said mixture is a mixture of bisglyceryl borate, {mono(monobutoxyethyl), di(-monomethoxydiethyleneoxyethyl)} borate, tetraethylene glycol monomethyl ether and pentaethylene glycol monomethyl ether.

8. A brake fluid composition for automobiles according to claim 1, wherein said mixture is a mixture of bisglyceryl borate, bissorbityl borate, {mono(-monobutoxyethyl), di(monomethoxytriethyleneoxyethyl)} borate and triethylene glycol monoisopropyl ether.

9. A brake fluid composition for automobiles according to claim 1, wherein said mixture is a mixture of bisglyceryl borate, bis(glyceryloxyglyceryl) borate, {poly(1.5 moles) (monobutoxyethyl), poly(1.5 moles) (monomethoxytriethyleneoxyethyl)} borate, monobutoxypoly(1.5 moles) propylene glycol poly (3.5 moles)ethylene glycol ether and triethylene glycol monoethyl ether.

* * * * *